United States Patent
Napolitano, Jr. et al.

(10) Patent No.: US 7,712,377 B2
(45) Date of Patent: May 11, 2010

(54) DIMPLE TEST FOR DETECTING IMPROPERLY INSERTED HOSE

(75) Inventors: Alfred D. Napolitano, Jr., Guelph (CA);
David William Ernst, Roseville (CA);
Ryan Everett Lebold, Kitchener (CA);
Jeffrey John Thomas, Mississauga (CA)

(73) Assignee: Bend All Automotive Incorporated, Ayr, Ontario (CA)

( * ) Notice: Subject to any disclaimer, the term of this patent is extended or adjusted under 35 U.S.C. 154(b) by 752 days.

(21) Appl. No.: 11/672,287

(22) Filed: Feb. 7, 2007

(65) Prior Publication Data

US 2008/0184824 A1    Aug. 7, 2008

(51) Int. Cl.
*G01N 3/08* (2006.01)
*G01N 3/48* (2006.01)
*F16L 33/00* (2006.01)

(52) U.S. Cl. .............. 73/818; 73/81; 285/256
(58) Field of Classification Search .......... 73/78, 73/81, 821, 865.8, 866, 818; 285/256
See application file for complete search history.

(56) References Cited

U.S. PATENT DOCUMENTS

| 2,121,624 | A | * | 6/1938 | Cowles | 285/256 |
|---|---|---|---|---|---|
| 2,797,111 | A | * | 6/1957 | Beazley | 285/222.4 |
| 3,367,683 | A | * | 2/1968 | Mattson | 285/243 |
| 3,850,029 | A | * | 11/1974 | Swanson | 73/81 |
| 3,883,938 | A | * | 5/1975 | Schmidt et al. | 29/715 |
| 4,004,457 | A | * | 1/1977 | Eide et al. | 73/818 |
| 4,106,526 | A | * | 8/1978 | Szentmihaly | 138/109 |
| 4,366,841 | A | * | 1/1983 | Currie et al. | 138/109 |
| 5,275,032 | A | * | 1/1994 | Gloe et al. | 72/19.8 |
| 6,095,571 | A | * | 8/2000 | MacDuff | 285/256 |
| 6,516,655 | B1 | * | 2/2003 | Adrian | 73/83 |
| 6,729,188 | B1 | * | 5/2004 | Boecker et al. | 73/821 |
| 7,121,136 | B2 | * | 10/2006 | Tsujii et al. | 73/81 |
| 7,212,720 | B2 | * | 5/2007 | Wied et al. | 385/139 |
| 7,338,090 | B2 | * | 3/2008 | Baldwin et al. | 285/256 |

* cited by examiner

*Primary Examiner*—Lisa M Caputo
*Assistant Examiner*—Punam Patel
(74) *Attorney, Agent, or Firm*—Anthony Asquith Corp (57) ABSTRACT

In a crimped hose, a length of rubber tubing is crimped into a blind-ended ferrule. To determine whether the tubing has been fully inserted, a dimple is pressed into the ferrule. The force needed to produce the dimple is small or large, depending whether the rubber is inserted properly, and the difference is large enough to serve as a detector. Measuring the dimple-force provides a commercially-useful test for proper insertion.

18 Claims, 4 Drawing Sheets

DIMPLE TEST FOR DETECTING IMPROPERLY INSERTED HOSE

This invention relates to hydraulic and other kinds of rubber hoses, and to the type of connection between a rubber tube and e.g a pipe or fitting in which the connection is made by crimping the hose in the annular space between a crimp-ferrule and the pipe.

BACKGROUND OF THE INVENTION

Often, in such joints, the crimp-ferrule is blind-ended, whereby it is impossible to see whether the tubing is fully inserted into the ferrule, neither before nor after the crimping operation has been carried out. The possible consequence of improper insertion of the rubber tubing into the ferrule is that the connection is liable to premature failure, i.e to leak, or even to burst apart.

It has been the traditional practice to provide a sight-hole in the crimp-ferrule, at or near the blind end thereof, for inspection purposes. The sight-hole, or witness-hole, provides a window through which an inspector can determine whether rubber is or is not present within. The sight-hole is located at a place where, if rubber is visible through the sight-hole, that fact is an indication that the hose has been fully, i.e properly, inserted.

It is notoriously difficult for even the most conscientious inspector, upon visually checking thousands of hose connections, to pick out the tiny fraction in which the rubber is not visible through the sight-hole. However, hitherto, it has not proved practically reliable to detect the presence or absence of rubber, through the sight-hole, by the use of automatic detection equipment.

The invention is aimed at providing, in a hose connection to a pipe or other fitting, a test for detecting whether the rubber tubing has been fully inserted into the ferrule. One aim is to provide a test that is operable automatically, and is highly reliable at detecting the difference between proper and improper insertion.

SUMMARY OF THE INVENTION

In the new test, a dimple is pressed into the ferrule. The force needed to make the dimple is measured, e.g by means of a load-cell, and the measurement is transduced to suitable detection equipment. It has been discovered that, if rubber is present underneath the dimple, the force needed to form the dimple is typically twice the magnitude of the force that is needed to form the dimple when rubber is not present underneath the dimple. It is recognised that this difference in force is adequate to serve as a test, to reliably distinguish between the presence of rubber and the absence of rubber.

It might, at first, be considered that the force needed to make a dimple in a (metal) ferrule would be largely independent of whether there was rubber present underneath the metal. However, tests have shown that the presence of the rubber is highly determinative as to what force is needed—so much so that the magnitude of the force can indeed serve as a reliable detector of whether the rubber tubing is present.

When the rubber tubing is crimped to the ferrule, in a crimp-press, it might be considered that it would be acceptable, instead of measuring the force needed to form a dimple in the ferrule, to measure the press-force needed to form the crimp. Thus, (where the press is hydraulic) a simple measurement of the hydraulic pressure would be adequate to detect whether the rubber tubing was present. It has been found that this is not so. The press-force needed to form the crimp often does indeed vary, depending upon whether the rubber is present or not—but it is recognised that the margin between the two cases is too small. There would be too many false positives and/or false negatives, for a test based on crimp-press-force to be regarded as commercially reliable.

By comparison, the magnitude of the force needed to produce the dimple has been found to have a more than adequate margin of difference between rubber-present and rubber-absent, to the extent that a test based thereon can indeed be commercially reliable.

Preferably, the dimple is made by a dimple-pin. Preferably, the dimple-pin is mounted in the crimp-tooling of the crimp-press. Thus, the dimple is formed in the same movement or stroke of the press that actually forms the crimp. This simultaneousness is an advantage. If the dimple were made prior to the crimp, it might be possible for a hose that was properly inserted during dimple-forming might have been displaced by the time crimping takes place. If the dimple were formed after the crimp, it might be difficult to correlate the fact of the hose being mis-inserted with the particular cause of the mis-insertion.

However, simultaneity is not essential. One alternative is an operable dimple-force-applying unit that is physically separate, and separately powered, from the crimp-tooling. The dimple-test is then applied as a separate operation from the crimp-stroke. In this alternative, the unit is powered by its own dedicated e.g hydraulic ram. Even then, preferably, the dimple-test is carried out while the hose components are still held in the crimp-tooling, for the reasons previously mentioned.

It is recognised that, inevitably, there are large tolerances both on the outside diameter of the hose and on the inside diameter of the crimp-ferrule. A hose-insertion-detection system has to be able to detect the difference between rubber-present and rubber-absent, with sufficient margin that, whether the tolerances are medium, or near the slack or tight tolerance extremes, that the particular tolerance situation does not affect the outcome of the test. It is recognised that the dimple-test as described herein, if done properly, can have a large enough margin between hose-fully-inserted and hose-not-fully-inserted to give freedom from the commercial problems arising from false positive and/or false negative results. It is recognised that measuring other parameters does not lead to such an adequate margin.

It has been found that the dimple-test, as described herein, can well detect the fault when the rubber extends only so far into the ferrule that the rubber only partially reaches underneath the dimple-pin, and the dimple-test can even more surely detect when the rubber does not reach the dimple-pin.

It is recognised that, in many cases, rather more of the force of crimping goes in deforming the rubber (and braid reinforcement) of the hose, than goes in deforming the metal of the crimping-ferrule. But, even with that recognition, it is not intuitive that a test to detect the presence of rubber underneath metal by deforming the metal would be sensitive enough for commercial use.

Traditionally, when designing a crimped hose joint, some designers have preferred to use a configuration of crimp-tooling in which the punches bottom or close together, as the means to determine the end of the crimp-stroke. Other designers have preferred a configuration in which the end of the crimp stroke is determined by the (hydraulic) crimp-press reaching a pre-determined hydraulic pressure. These two different configurations can be referred to as the punches-close or "bottoming" configuration, as against the punches-do-not-close or "non-bottoming" configuration.

It has been found that the dimple-test as described herein is very effective at detecting when the rubber tubing has not been inserted fully, and at avoiding false positives and/or false negatives, particularly in the punches-close case. It has been found that the margin is not quite so large when the crimp-tooling is of the punches-do-not-close configuration—however, even though the margin is smaller, it is recognised that the margin can still be adequate to serve as the basis for a commercially reliable test, in the punches-do-not-close configuration.

A problem can sometimes arise in the punches-do-not-close configuration. In the event that the tubing is only partially inserted, still the hydraulic pressure in the rams of the crimp-press continues to increase towards the predetermined limit of pressure. But now, the portion of the rubber tubing which is partially inserted takes all the force. So, what can happen is that this portion of the rubber can become crushed and distorted to the extent that the reinforcing braids in the rubber tubing can be broken. The thus-made improper connection is much more liable to fail—but the problem is that the improper connection might well not differ in appearance very much from a proper connection. By contrast, the problem of ruptured braids largely does not arise with punches-close tooling. Thus, important as it is to detect badly-inserted tubing when using punches-close tooling, it is even more important to detect an improper connection in punches-do-not-close tooling.

Preferably, the dimple-pin pushes the rubber at a location outside, or away from, the crimping-punches. However, pressing on the crimped area can give a commercially-useful difference between rubber-present and rubber-not-present, particularly in punches-close tooling.

BRIEF DESCRIPTION OF THE DRAWING

Examples will now be described, with reference to the accompanying drawings, in which.

DETAILED DESCRIPTION OF THE INVENTION

The apparatuses and procedures described herein and depicted in the accompanying drawings are examples. It should be noted that the scope of the patent protection sought is defined by the accompanying claims, and not necessarily by specific features of the examples.

Figure 1:
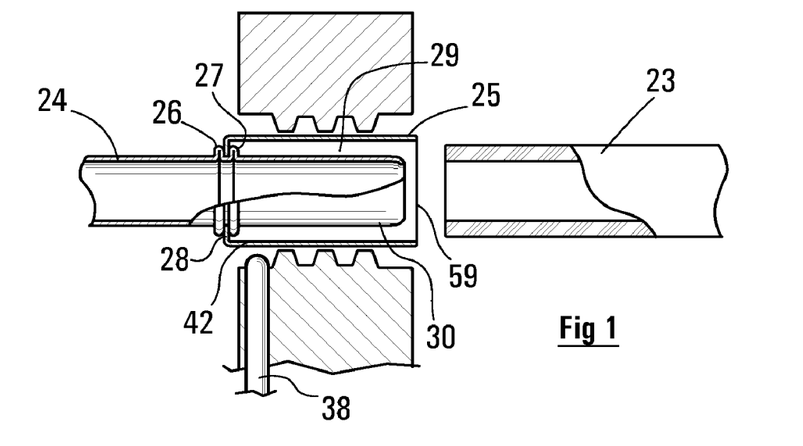
FIG. 1 is a cross-section of some components of a crimp-press, having punches-close crimp-tooling, in which rubber tubing is about to be crimped to a pipe.
Figure 2:
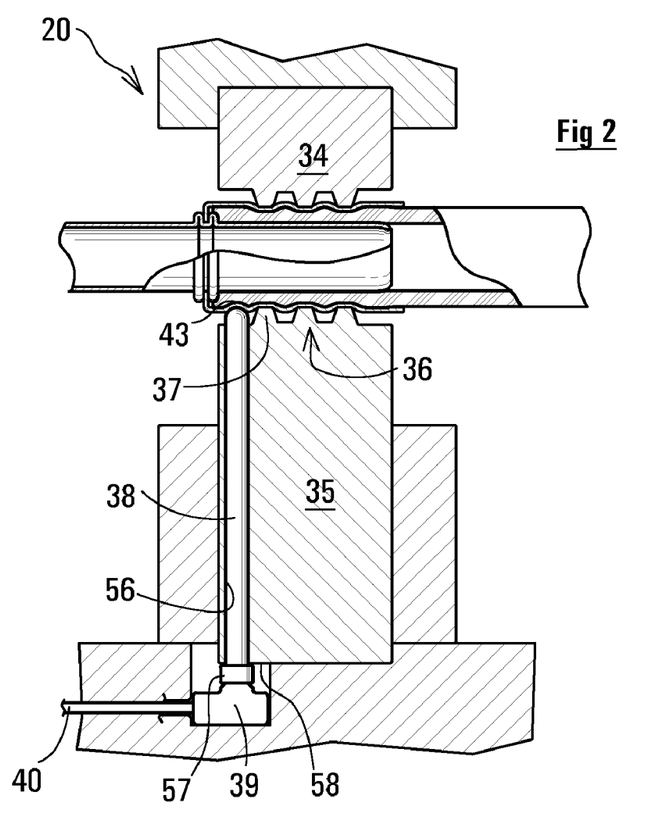
FIG. 2 is the same view as FIG. 1, in which the crimping operation is being carried out.

FIGS. 1, 2 show a crimp-press 20, in which rubber tubing 23 is being crimped onto a pipe 24. The pipe 24 has been prepared for the hose-crimping operation in that a crimp-ferrule 25 has been lock-beaded to the pipe 24. To do this, first an abutment-bead 26 was formed in the pipe 24 (by pressing the pipe axially from the end in a suitable die); then the crimp-ferrule 25 is laid against the abutment-bead 26; then a lock-bead 27 is pressed into the pipe 24, snagging the flange 28 of the crimp-ferrule 25, and locking the assembly firmly together.

The intention is that the rubber 23 be inserted fully, i.e as far as it will go, into the annular space 29 between the crimp-ferrule 25 and the nose-end 30 of the pipe 24, towards the blind far end of the space 29. The dimple-test determines whether the rubber tubing has been inserted fully.

In FIG. 2, the tubing 23 has been fully inserted, and the crimping operation has been carried out. That is to say, the crimp-punches 34,35 have squeezed the crimp-ferrule 25 into the rubber. The crimp-punches 34,35 are components of a set of (typically) six crimp-punches, which are disposed radially around the crimp-ferrule. The press is arranged to press all six crimp-punches radially inwards simultaneously, in the crimping operation. Each crimp-punch is formed with an appropriate set 36 of crimp-teeth, which deform the crimp-ferrule 25 radially inwards.

After the crimp-ferrule 25 has been squeezed by the crimp-press 20, the resulting deformation of the crimp-ferrule is sufficient to hold the rubber 23 in a compressed state, to provide a mechanically secure, hydraulically sealed, connection.

The crimp-ferrule 25 is typically made of thin aluminum (or thin steel), and is readily deformable. Typically, the force needed to deform the metal is hardly more than the force needed to squeeze the rubber 23. Of course, after the crimping forces are released, there will be some spring-back of the crimp-ferrule 25, and the designer should see to it that the crimp-ferrule has enough strength and rigidity that this spring-back still leaves the rubber firmly secured and sealed.

The press 20 includes a dimple-pin 38, and a load-cell 39. The dimple-pin rests on, and is supported on, the load-cell. That is to say, when the dimple-pin 38 is pressed downwards (in FIG. 2) the dimple-pin 38 is prevented from moving downwards by its abutment against the load-cell 39. The load-cell measures the force with which the dimple-pin is being pressed downwards. A cable 40 carries the electrical signals from the load-cell 39 away from the crimp-press 20 to a suitable signal reader such as a computer.

During the crimping operation, as the respective sets 36 of crimp-teeth on the crimp-punches are squeezed onto the crimp-ferrule 25, the dimple-pin 38 makes a recess or dimple 43 in the metal of the crimp-ferrule 25.

It will be noted that, in FIG. 2, the dimple-pin 38 lies, with respect to the entry mouth 59 of the crimp-ferrule 25 into which the tubing 23 is inserted, beyond the furthest 37 of the set 36 of three crimp-teeth. When the dimple-pin 38 is positioned beyond the furthest tooth (i.e to the left, in FIG. 2), the dimple-pin 38 acts on the furthest portion 42 of the crimp-ferrule 25, being a portion that is left untouched by the crimping operation itself. This is the preferred position, in that now the dimple-pin is far enough beyond the crimp-teeth that the level of force required to make the dimple 43 is unaffected by the disturbance and distortion of the ferrule caused by the crimping operation.

The force in the dimple-pin 38 varies in accordance with the presence or absence of the rubber 23 within the deepest portion 42 of the crimp-ferrule 25. It has been found that, if the rubber tubing 23 is not present inside the deepest portion 42, i.e if the rubber tubing has not been fully inserted into the annular space 29, the force needed to form the dimple 43 is typically less than half the corresponding force needed to form the dimple when the tubing 23 has been fully and properly inserted.

It is recognised that this magnitude of difference provides a very reliable manner of detecting whether or not the rubber tubing has been inserted properly.

Figure 3:
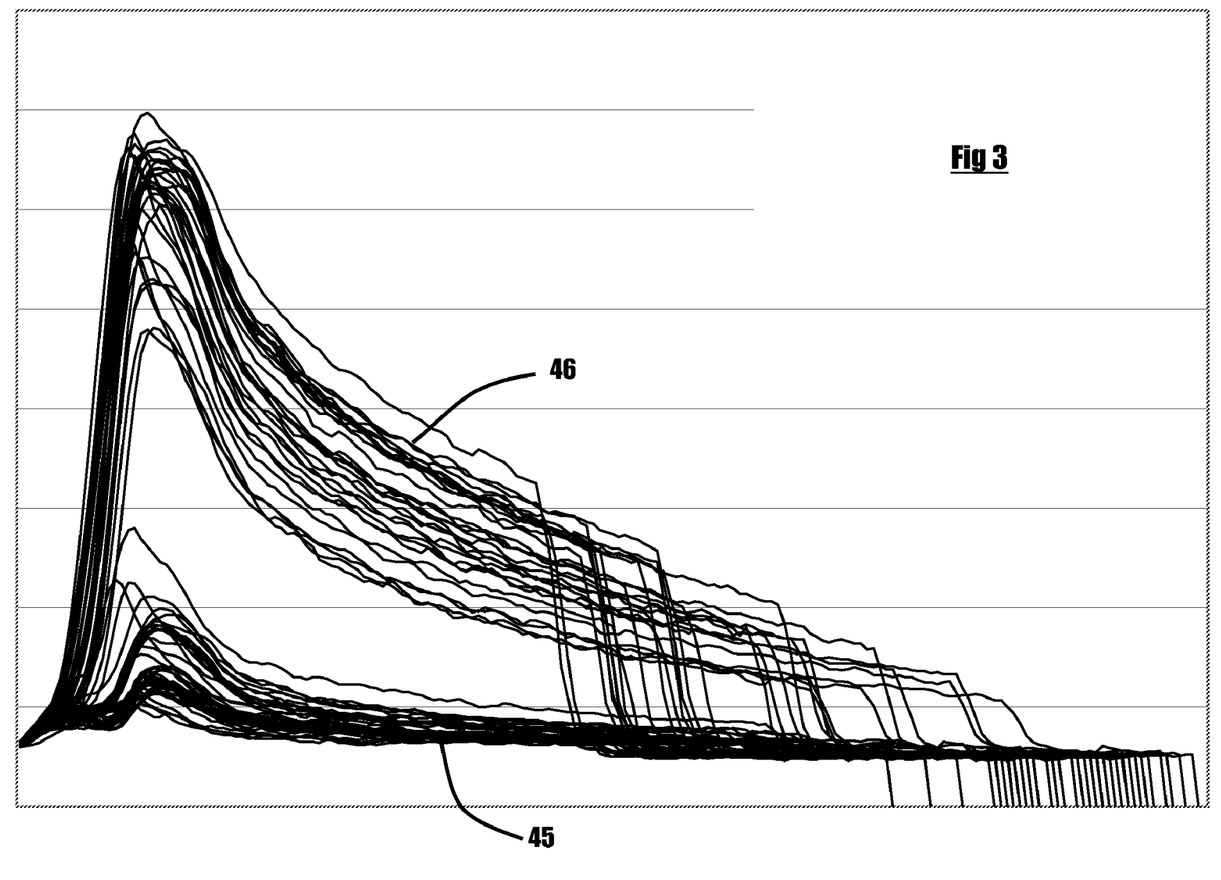
FIG. 3 is a graph showing the force in a dimple-pin of the crimp-press of FIGS. 1, 2 under different circumstances.

FIG. 3 is a printout of a series of output traces from the load-cell 39, made under various circumstances. The traces record dimple-force on the y-axis, versus time on the x-axis. In the traces indicated by numeral 45, the rubber tubing was not properly inserted. These several traces represent variations in the extent of the mis-insertion, and traces were obtained using different dimensional-tolerance conditions.

The rubber tubing 23 was properly inserted in the traces indicated by numeral 46. Again, in these traces 46, the extent of the proper insertion was varied, and again traces were obtained using different dimensional-tolerance conditions.

It may be observed in FIG. 3 that the highest magnitude of the peak force encountered in any of the not-full-insertion traces 45 is barely half the lowest magnitude of the peak force encountered in any of the full-insertion traces 46.

Figure 4:
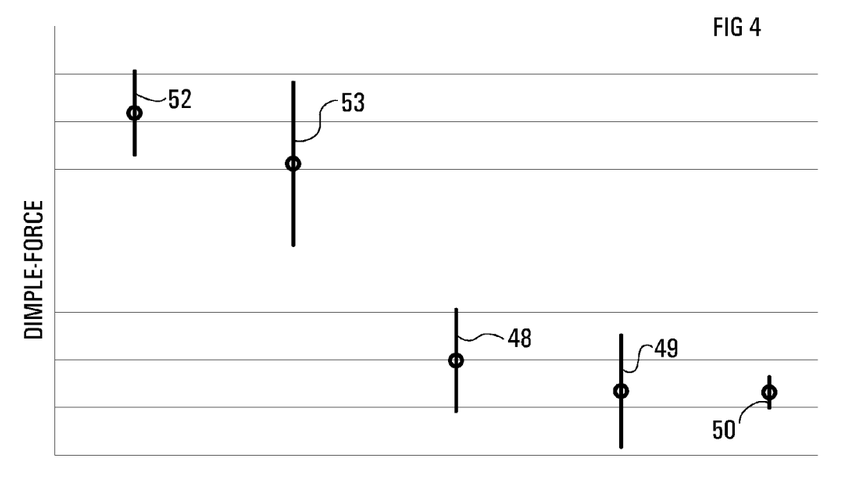
FIG. 4 summarises some of the statistical parameters of the forces derived from FIG. 3.

FIG. 4 shows the statistical spread of the traces. The vertical bars in FIG. 4 indicate the peak forces reached by the load-cell 39 during crimping, in the several traces corresponding to the conditions as indicated. (It should be noted that the traces were not calibrated to actual force units; in other words, the traces indicate merely the changes in voltage output, voltage being proportional to force in the load cell.) The circle in the middle of the bar is the average of the several peak forces, and the length of the bar is set at plus/minus three standard-deviations away from that average.

In FIG. 4, bars 48,49,50 refer to less-than-full insertion, while bars 52,53 refer to full insertion. The large gap between the lowest point on the "full" bars 52,53 and the highest point on the "less-than-full" bars 48,49,50 will be readily apparent. Thus, it is a simple matter to calibrate the difference in the load-cell reading that will reliably detect the difference between properly inserted tubing and badly inserted tubing, and will produce a reliable accept/reject signal.

Figure 6:
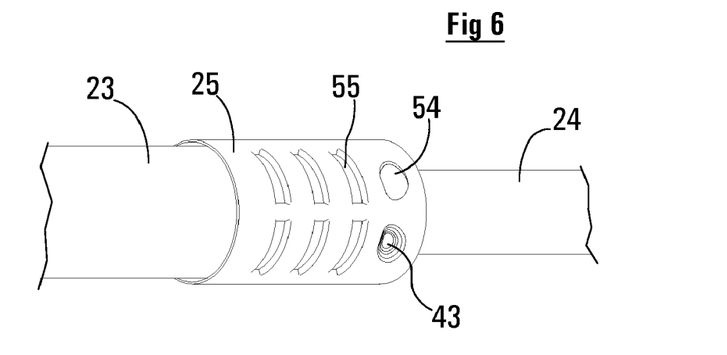
FIG. 6 is a diagrammatic pictorial view of a crimped hose.

The bar 48 shows the dimple-force when the rubber tubing was inserted so that it was just showing in the sight-hole 54 (FIG. 6). For the bar 49, the tubing was inserted short of the third crimp tooth 37. In both bars 48 and 49, the tolerances were set at the nominal fit of the tubing within the ferrule. In bar 50, the tubing was again inserted short of the third crimp tooth 37, but here the tolerances were set at the tightest tolerated fit of the tubing in the ferrule.

The associated systems can readily be designed to process the data and produce the signal automatically on a mass-production line. The associated systems can be designed to stop the production line upon detecting that the tubing has not been inserted properly, i.e upon issuance of a not-go signal. Where the rubber tubing 23 is inserted into the crimp-ferrule 25 by automatic machinery, stopping the line will usually be preferred, because poor-insertion (or non-insertion) probably means that a fault has developed in the automatic machinery, which needs to be corrected before production continues. In a case where the rubber tubing is inserted manually by a human operator, it is probably sufficient for the reject signal to trigger a simple alarm.

Figure 5:
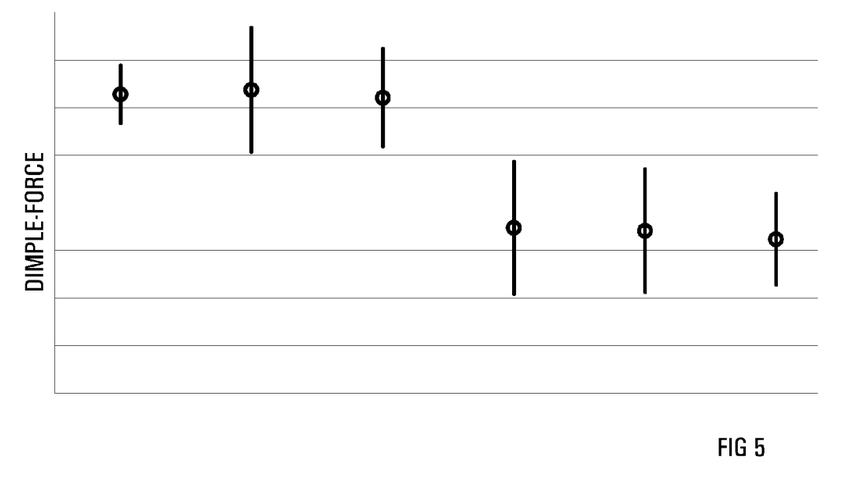
FIG. 5 is a graph like FIG. 4, but using punches-do-not-close crimp-tooling.

FIG. 5 is a similar diagram to FIG. 4, except that now the crimp-tooling is in punches-do-not-close, or non-bottoming, configuration. It can be seen that the difference between accept and reject is not quite so distinctive and decisive as was the case in FIG. 4. But even so, the difference is still perfectly adequate to serve as the basis for an automatic mass-production test procedure. Thus, the dimple-test may be used whether the crimping has been done in punches-close or in punches-do-not-close crimp-tooling.

In FIG. 5, the first three (upper) bars show the dimple-force when the tubing has been fully and properly inserted, in the nominal, tightest, and slackest, fits respectively. For second three (lower) bars, the tubing was inserted short of the third crimp tooth, again in the nominal, tightest, and slackest, fits respectively. It will be noted from these results that differences in dimple-force due to tolerances in the fit between rubber and ferrule are of little significance, but the differences in dimple-force between full and partial insertion is quite decisive. In FIGS. 4, 5, the force units are not recorded, except that the bottom line of the graphs does represent zero force. The two figures are not drawn to the same scale of force.

The production engineer does not need to carry out very much by way of preliminary experiments or tests, in order to determine the level of force at which to set the trigger for the alarm signal. Most of the hose crimps created in a mass-production run will be good, whereby, on a given production batch, a statistic can quickly be built up of the average force, and the spread of forces, needed when producing a good crimp. The engineer simply arranges that if the crimp force should happen to differ from the average crimp force by more than, say, four standard-deviations, the alarm would be signalled. Of course, false positives and false negatives can never be completely ruled out, but it will be appreciated that a complete absence of false readings can be very closely approximated, with only a little (initial) input from the engineer or toolsetter, and with no input at all from the production line workers and inspectors.

It should be noted that the large (three or four standard deviations) differences in the dimple force, between the rubber-properly-inserted and the rubber-not-properly-inserted conditions are not necessarily essential to the accept/reject decision. Sophisticated statistical analysis, including mapping of trends, picking out of sudden changes, etc, can be used to sort out when a hose should be rejected. That is to say, the dimple force measurements from very many crimped hoses are useful for generating more than just the average value and the deviation value. The designer might e.g arrange for recordation and analysis of the shape of the dimple-force traces (like those of FIG. 3)—it has been found that, if the rubber is only partially inserted into the ferrule, the shape of the peak of the trace is usually quite different, even if the peak force level might be not hugely different, and that shape can be used to contribute to the decision whether to accept or reject the hose. Also the rate of rise of the force can contribute to the decision.

The tubing and the ferrules will typically be placed into the crimp-press by automatic tube-handling tooling. One possible problem might arise, for example, in that this feed-tooling starts to feed gradually less of the end of the rubber tubing into the ferrules, whereby the tubing is now not being pushed fully quite all the way into the ferrule. That fault would show up as a trend, e.g a trend of the gradual dropping-off of the dimple force. Thus, a gradual but maintained trend should trigger an investigation. And a sudden, though small, change likewise should trigger an investigation. The point is that, using the dimple-force sensing system as described, in which the actual force on the dimple sensor is automatically measured and recorded, every crimp, more and more sophisticated statistical algorithms can be developed on an ongoing basis, which will enable the ideal to be (almost) realised, of passing every single hose that is correctly crimped, and of rejecting every single hose that is wrongly crimped—and, indeed, of reducing or eliminating the incidence of wrongly-crimped hoses.

FIG. 6 shows a completed crimped hose. The crimp-teeth 34,35 have produced crimped-indentations 55 in the ferrule 25. The dimple-pin 38 has produced the dimple 43, which also is indented into the ferrule 25.

Hitherto, it has been traditional practice to provide a sight-hole 54 in the crimp-ferrule 25, near the flange end 28 of the crimp-ferrule—i.e, in the deepest portion 42 of the crimp-ferrule, beyond the endmost crimp-tooth 37. The idea of the sight-hole was that if the rubber tubing had been inserted properly, it would be visible in the sight-hole. It might be preferred still to provide the sight-hole 54, even when using the dimple-test described herein. If a hose failure occurs, it might be desired, without cutting the joint apart, to be able to tell whether the joint had been crimped properly, and the sight-hole 54 provides a simple and non-destructive manner of indicating whether the tubing 23 was fully inserted. (The disadvantage of the sight-hole is that it relies on ongoing human visual observation, which has a greater fallibility than can be tolerated for production-line inspection. But if a failure has occurred, now there will be time for a thorough examination, and the sight-hole enables the engineer to quickly establish that the crimp was or was not to blame.)

The sight-hole 54 does have its disadvantages, however, in that (a) it is quite awkward (and therefore costly) to provide tooling to punch the sight-hole in the ferrule 25; (b) if a joint is less than perfect, the sight-hole provides a shorter leakage path for liquid to leak out of the joint; and (c) the sight-hole preferably should be located where it cannot interfere with the dimple 43, and that can be difficult since space is tight.

The location of the dimple-pin 38 will now be further considered. In crimp-tooling, where there are typically four or six individual crimp-punches that are pressed together radially, it is common for one of the crimp-punches (35 in FIG. 2) to be held stationary with respect to the frame of the crimp-press 20, and for the rest of the crimp-punches to move relative to that one fixed crimp-punch 35. Thus, in FIG. 2, the lower crimp-punch 35 is held stationary, and the upper crimp-punch 34 (and the rest of the crimp-punches, which are not shown in FIG. 2) would be activated in some suitable manner for driving all the crimp-punches radially inwards, in unison.

The dimple-pin 38 preferably is mounted in the stationary crimp-punch 35, and preferably in the manner as shown in FIG. 2. However, mounting the dimple-pin in one of the moving crimp-punches 34 is not insurmountably difficult, and in some configurations of crimp-tooling that might be preferred. In fact, the designer may choose to provide two or more dimple-pins, rather than just one, including two dimple-pins in crimp-punch 35, and/or further dimple-pins in the movable crimp-punches.

As mentioned, users of crimped hoses might prefer that the sight-hole still be included, even though the dimple-test as described is performed—because the sight-hole is traditional, and because it does enable the end user actually to see that the rubber has been inserted properly. However, if a sight-hole is provided, and if the dimple pin should happen to be aligned with the sight-hole during the dimple test, then of course the dimple-force will be very low, and will likely indicate (wrongly) that the rubber is absent. Therefore, the designer should in that case provide two dimple pins, spaced circumferentially around the ferrule. There is only one sight-hole, so it is easy to ensure that, if one dimple pin should happen to be aligned, or be even nearly aligned, with the sight-hole, the other dimple pin is bound to be well clear. If there is room, the sight-hole can be spaced axially from the area that is subject to being dimpled, and in that case, only one dimple would be required.

The dimple-pin 38 in FIG. 2 is shown as being movable relative to the crimp-punch 35. Alternatively, the dimple-pin 38 can be mounted in, and can be made movable relative to, the crimp-punch-holder 55.

From a perusal of FIG. 2, it will be understood that, although space is, of course, very tight in the crimp-tooling, there is ample room for the dimple-pin 38. This is because the dimple-pin is (preferably) a slender, straight, right-cylindrical rod, which is guided and constrained within a right-cylindrical pin-hole 56 in the solid bulk of the crimp-punch 35. Supported thus, the dimple-pin 38 can transmit even quite large forces, over the distance needed to reach an area where space is at less of a tight premium, where the load-cell 39 can be accommodated. The pin-hole 56 can be a sufficiently loose clearance that there is no chance of the dimple-pin 38 jamming therein, and yet the constraint provided by the hole prevents the long dimple-pin from buckling under the load. In typical crimp-tooling, the length of the dimple-pin 38 would need to be about three cm, or more, to be far enough away from the working die surfaces for the designer to provide enough room to accommodate the load-cell. In the example depicted in FIG. 2, the dimple-pin 38 was six cm long.

The dimple-pin 38 is provided with a head 57 at its lower end. The load-cell 39 should be assembled and positioned at such a height, in the crimp-punch 35, that the dimple-pin resides with its head 57 abutting against the surface 58 of the crimp-punch 35.

The load-cell 39 must, of course, be of a capacity such that the load-cell can support the loads to which the dimple-pin is subjected, as it is driven into the crimp-ferrule 25, and creates the dimple 43, during the crimping stroke. The (passive) load-cell 39 is not absolutely rigid and solid—of course, it is the physical deflection of the load-cell that serves as the measurement of the force on the load-cell—but the load-cell should be solid enough that the dimple-pin can drive into the crimp-ferrule, and can compress the rubber underneath, without itself undergoing a significant deflection. It can be expected that a simple passive load-cell, properly selected, will have enough rigidity to enable the dimple-pin to create a proper dimple.

Active load-cells (i.e load-cells that are powered, or servo-operated, and which have literally zero deflection) can alternatively be used. These are expensive, and more difficult to find room for, to install, to set up, and to operate, but they can be used if the deflection attributable to a passive load-cell were a problem.

As mentioned, in FIG. 2, the dimple-pin 38 lies, with respect to the entry mouth 59 of the crimp-ferrule 25 into which the rubber tubing 23 is inserted, beyond the furthest 37 of the (three) crimp-teeth. This is the preferred position, in that now the dimple-pin is far enough from the crimp-teeth that the level of force required to make the dimple 43 is unaffected by the disturbance and distortion of the ferrule caused by the crimping operation.

Figure 7:
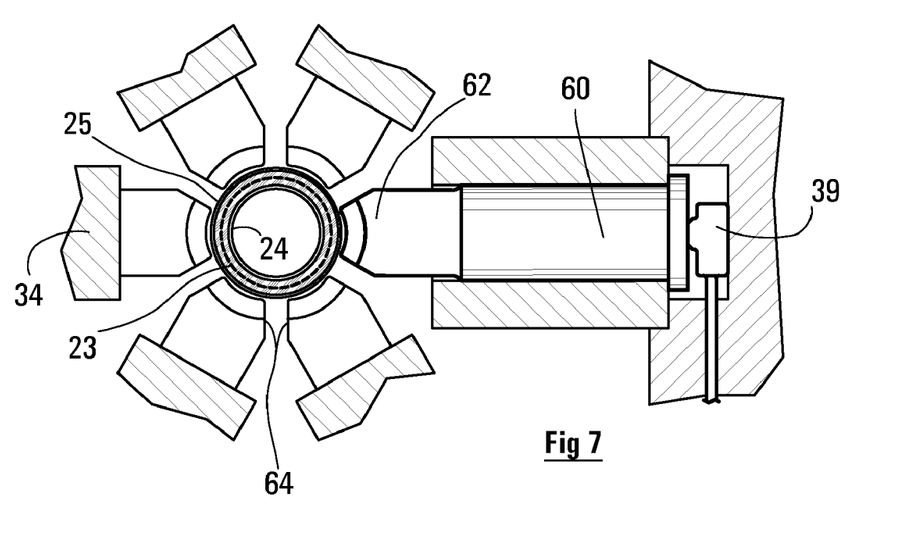
FIG. 7 is an end-elevation of components of another crimp-press having punches-close crimp-tooling.

Alternatively, as shown in FIG. 7, the dimple-pin 60 may be combined with the furthest crimp-tooth 62. Now, the dimple-pin and the crimp-tooth are unitary, and incapable of relative movement as in FIG. 2. The crimp-tooth 62 is formed on the end of the long slender dimple-pin 60, which is supported on the load-cell 39. Alternatively again, the dimple-pin may be combined with a crimp-tooth other than the furthest crimp-tooth 62, although that is not preferred if the test is intended to detect the difference between proper and improper insertion.

One difficulty that might arise when the dimple-pin is combined with one of the crimp-teeth is that the shape and position of the dimple-pin might have to be compromised by the need to combine two functions, whereby the measurement of the force on the dimple-pin is not so decisive and definitive of the completeness of the insertion of the rubber tubing. On the other hand, combining the dimple-pin with one of the crimp-teeth does save space. As mentioned, it might be preferred to keep the traditional sight-hole, as a back-up, in addition to carrying out the dimple-test, and combining the dimple-pin with one of the crimp-teeth does leave room for the sight-hole.

The crimp-tooling shown in FIG. 7 is punches-close tooling, in that the six individual crimp-punches, of which punch 62 is one, are all pressed radially inwards, thereby compressing the ferrule onto the rubber. The crimp-punches move inwards until all are touching, i.e are touching at their side-faces 64. The crimp-tooling is now closed. After that, any further radial force applied to the crimp-punches will be reacted internally between the crimp-punches, and will not be transmitted to the ferrule nor to the rubber.

One of the benefits of the dimple-test using a separate dimple-pin 38 as in FIG. 2 is that the presence of the dimple 43 is very readily apparent, so it is easy for the inspector to determine that the crimped joint has been tested. One of the disadvantages of combining the dimple-pin with one of the crimp-teeth, as in FIG. 7, might be that an inspector cannot tell, simply from looking at the joint, whether the test has been done.

Rubber hoses are sometimes crimped, not to a length of pipe, but directly to a screw-threaded or other type of metal fitting. The crimp-ferrule must still be crimpable, of course, but the ferrule probably would not then be attached to the fitting by lock-beading, as in FIGS. 1, 2, but in some other manner. The use of the dimple-test as described herein would still be advantageous, in that case.

Sometimes, the crimp-ferrule is not attached directly to the pipe or fitting at all. That is to say, the crimp-ferrule is simply an open-ended length of metal tubing. Often, in that case, it can be simply determined visually that the rubber has been properly inserted, by noting that the rubber does indeed protrude from the far end of the ferrule—in which case the dimple-test as described might be superfluous. However, even when the insertion is done to an open end (i.e a through-end), rather than a blind end, the need might arise for an automatic test to determine proper presence of the rubber, beneath the ferrule, and again the dimple-test can be used in that case. The presence of the dimple automatically indicates that the test has been done. (In traditional ways of testing, the performance of the test might leave no mark at all, and it might be left to an operator to apply a dab of paint, for example, to the finished hose, to indicate that the test has been done.)

The dimple test as described herein can be applied generally to rubber hoses that have a metal ferrule as part of an end fitting. The test is most convenient when the ferrule is crimped inwards, in order to secure (and seal) the rubber tubing to the metal ferrule. The test is applicable irrespective of the nature of the fluid being conveyed through the hose.

It should be noted that the dimple-test is particularly applicable when the hose is intended for conveying fluid under comparatively low pressures. The reason lower pressure applications are preferred is that, if the hose is intended to carry higher pressures, the ferrules are made of thicker metal—and, the thicker the metal, the more force that is needed to put a dimple in the metal, and therefore the smaller the margin of difference in the dimple-producing force between when the rubber is present and when the rubber is absent. Thus, a hose rated at a burst pressure of, say, 5000 psi would likely have a ferrule of metal that was so thick and stiff that the difference between rubber-present and rubber-not-present conditions might not be distinguishable reliably by the as-described dimple-test. It can be expected that the very reliable results as described herein can be achieved in the case of hoses with a rated burst pressure up to say 1000 psi. Low-pressure hoses—with rated burst pressures up to, say, 50 psi—are not normally manufactured with crimped ends, but if they are, their mass-production can be made more economical by the use of the dimple-test as described.

The dimple-test as described can also be used with double-ended hoses, in which both ends are crimped at the same time. Rubber-insertion faults might be linked between the two ends (e.g, a hose that is too tight at one end might be too loose at its other end). Preferably, both ends should be dimple-tested.

As described, the main function of the dimple test, as described herein, is to determine whether the end of the rubber tubing is fully inserted, right into the ferrule, at the moment of crimping. It should be noted that the dimple test can sense not just a reduced force, but also can sense too much force. Thus, the test can be used to indicate that the ferrule e.g has become buckled, or e.g two ferrules might have been accidentally locked onto the end of the pipe.

As mentioned, it has been noted, in tests, that there is a large difference in the dimple force between the fully-inserted rubber and the partially-inserted rubber. This difference may be further commented upon as follows.

One of the effects of crimping is, of course, to compress the rubber radially inwards in the area of the crimps. As the rubber is compressed radially, it expands lengthwise, and thus the rubber right at the end of the tubing tends to expand into, and in fact to fill, the volume or pocket at the blind end or flange end 28 of the ferrule, beyond the furthest crimp 37. The available volume of the pocket, for the rubber to expand into, is very small if the rubber tubing has been fully inserted. Thus, rubber trapped in the pocket, if the tubing has indeed been fully inserted into the ferrule, has "nowhere to go". Therefore, when the dimple sensor drives into the ferrule, over the pocket, the rubber within the pocket now enters a bulk-compression condition, whereby resistance of the rubber to further compression becomes much greater.

On the other hand, if the end of the rubber tubing has not been inserted properly to the very end of the ferrule, the rubber, upon being crimped, might not expand enough to fill the blind pocket, and therefore the rubber will not enter the bulk-compression condition when the dimple is formed. One of the reasons the difference between the full-insertion-dimple-force and the partial-insertion-dimple-force is so large thus is, or might be, this difference between bulk compression (in which the rubber must undergo a reduction of its volume) and normal distortion (in which the volume of the rubber substantially does not change). It is noteworthy that it is not so important that the difference between the partial-insertion-dimple-force and the zero-insertion-dimple-force should be large, since both those conditions are cause for rejection; it is the difference between the partial-insertion-dimple-force (and even between the almost-but-not-quite-full-insertion-dimple-force) and the full-insertion-dimple-force that is required to be large; and, as explained, the bulk-compression effect contributes to making that a large difference.

It is not essential that the dimple-pin be right-cylindrical. The cross-sectional profile of the dimple-pin can be non-circular, for example. The impression or dimple produced by the dimple-pin can be e.g slot-shaped, or be otherwise non-round. The dimple need not be round-ended, although that is preferred. Sharp edges preferably should be avoided. The dimple-pin preferably should be engineered to coordinate with the crimp-tooling such that the dimple-pin makes a permanent indentation in the metal of the ferrule, i.e such that the metal in the path of the dimple-pin is stressed beyond its yield point. A non-permanent deformation of the metal likely would not be at a high enough force level for the measurement of the force to distinguish between the rubber-present and rubber-not-present conditions. Also, a permanent deformation leaves a visible proof that the test has been done. Similarly, the indentation should be small in area, so that only a small force is needed, to produce enough stress in the metal to cause permanent deformation. In FIG. 2, the dimple-pin was about three mm in diameter, and the load-cell measured a force in the region of one kN; in FIG. 7, in which the dimple-pin is combined with the crimp-punch, the force in the load-cell would be nearer three kN.

It might be possible for the designer to arrange that the dimple-pin should puncture right through (i.e make a hole in) the ferrule. That is less preferred, because the force required to punch a hole in the ferrule is generally larger than the force required to produce simply an indentation dimple in the ferrule, and it is the fact that the force needed to make the dimple is small that makes the difference between the rubber-present dimple-force and the rubber-not-present dimple-force so decisive. However, with some kinds of hose, making a through-hole might be acceptable and should not be ruled out. That being so, the scope of the expression "dimple" includes "through-hole".

In this specification, the word rubber is used in a broad sense, to indicate a flexible elastomeric material. The raw material from which the rubber hose is manufactured can be, or can include, natural rubber. The raw material also can be, or can include, a synthetic elastomeric material. It is almost universal for hose rubber to include reinforcement in the form of textile fibres and the like. As far as the rubber material is concerned, if the hose rubber is suitable for crimping, then the dimple test as described herein may be performed.

The rubber tubing should be a reasonably tight fit inside the inside diameter of the ferrule. The dimple-test itself does not need an interference fit, but the requirements of the hose or the crimping process might require that kind of fit. The dimple-test does require, of course, that the tubing be tight enough that forming the dimple actually does compress the rubber.

As described, an aim of the dimple-test is to distinguish the rubber-present dimple-force from the rubber-absent dimple-force. The size of the batch should be such that the number of hoses mass-produced in the batch is large enough for the difference between the two conditions to be plotted and calibrated in terms of the difference in dimple-force. As mentioned, the rubber-present dimple-force and the rubber-not-present dimple-force is typically so large that the difference is simply unmistakable, even taking account of the different tolerance conditions. In statistical terms, the difference can be said to be (virtually) unmistakable when the rubber-absent average plus three standard deviations is less than the rubber-present average minus three standard deviations.

The engineer will usually prefer to apply the dimple-test to every single one of the hoses in a mass-production batch. When the dimple-pin and associated sensors are built into the crimp-tooling, and are operated on the same crimp-stroke as the crimp itself, the test costs nothing in terms of time spent per hose. Where the result of the dimple test is in electronic form, it is a very simple matter to record not only the peak force reached when forming the dimple, but also the profile or trace of the rise and fall of the dimple-force, which can be useful in picking out faults or highlighting trends. The records can be kept indefinitely.

LIST OF REFERENCE NUMERALS 20 crimp-press
23 rubber tubing
24 pipe
25 ferrule
26 abutment bead
27 lock bead
28 flange
29 annular space
30 nose end
32 blind end
34 upper crimp punch
35 lower crimp punch
36 crimp teeth
37 tooth
38 dimple-pin
39 load-cell
40 cable
42 furthest point of ferrule
43 dimple
45 improper traces
46 proper traces
48 bar
49 bar
50 bar
52 bar
53 bar
54 sight-hole
55 crimp
56 pin hole
57 pin head
58 head surface (of 35)
59 entry mouth
60 dimple-pin
62 furthest crimp tooth
64 punch side face.

The invention claimed is:

1. Test procedure for use in mass-producing a batch of hoses, one after another, where the hoses comprise respective lengths of elastomeric tubing and respective hollow metal ferrules;
   the test procedure is effective to determine, on a hose-by-hose basis, whether the tubing is properly present inside the ferrule, and includes:
   pressing a dimple inwards into the metal of the ferrule, in such manner as to make an indentation in the metal;
   providing a dimple-force measuring-device, and measuring the force needed to form the dimple, termed the dimple-force;
   determining a threshold value for the dimple-force;
   making an assessment, in respect of the individual hoses, whether the dimple-force is above or below the threshold; and
   accepting those hoses of the batch in respect of which the dimple-force is above the threshold, and rejecting those hoses of the batch in respect of which the dimple-force is below the threshold.

2. As in claim 1, including providing a dimple-pin, and applying the dimple-force to the ferrule by pressing the dimple-pin into the ferrule.

3. As in claim 2, wherein the dimple-pin is right-cylindrical and round-ended.

4. As in claim 2, including:
   providing a crimp-press, for crimping the ferrule to an end of the elastomeric tubing, to form the hose;

providing, in the crimp-press, crimp-tooling, which includes a plurality of crimp-punches;

so arranging the crimp-tooling that operating a crimp-stroke of the crimp-press is effective to drive the crimp-punches inwards together, thereby crimping the metal ferrule onto the elastomeric tubing, and thereby permanently deforming the metal of the ferrule inwards, and thereby producing hydraulic sealing and mechanical securement of the hose as a unit;

placing the metal ferrule in the crimp-tooling;

inserting the elastomeric tubing into an open end of the ferrule;

then operating the crimp-stroke; and then removing the resulting crimped hose, as a unit, from the crimp-tooling.

5. As in claim 4, including so arranging the dimple-pin in the crimp-tooling that operating that same crimp-stroke of the crimp-tooling is effective also to apply the dimple-force to press the dimple-pin into the ferrule of that same hose.

6. As in claim 4, including so arranging the crimp-tooling that the dimple in the metal is physically spaced apart from the deformation of the metal arising from the crimp-punches.

7. As in claim 4, including so arranging the crimp-tooling that the dimple-pin is functionally incorporated into one of the plurality of crimp-punches, termed a dimple-crimp-punch, in that the dimple-pin is pressed inwards into the ferrule in unison with the dimple-crimp-punch, during operation of the crimp-stroke.

8. As in claim 4, including arranging the crimp-tooling in a dies-close configuration, in which, during the crimp-stroke, the crimp-punches travel inwards until the crimp-punches reach a mechanical stop, which constrains the crimp-punches against further movement inwards.

9. As in claim 4, including arranging the crimp-tooling in a dies-do-not-close configuration, in which, during the crimp-stroke, the crimp-punches travel inwards until the force pushing the crimp-punches inwards reaches a predetermined maximum.

10. As in claim 1, including, the ferrule being closed- or blind-ended, inserting the elastomeric tubing right to the blind- or closed-end of the ferrule.

11. As in claim 10, including:

providing the ferrule with a sight-hole, right through the metal;

so placing the sight-hole that, if the elastomeric tubing has been properly inserted into the ferrule, the tubing is visible through the sight-hole.

12. As in claim 11, including forming, in addition to the said dimple, also a second dimple in the same ferrule, so pitched around the circumference of the ferrule from the said dimple that if one of the dimples coincides with the sight-hole, the other does not.

13. As in claim 1, including providing the dimple-force measuring-device in the form of an electronic load-cell, which sends a signal indicative of the dimple-force to a computer.

14. As in claim 13, including determining the threshold value for the dimple-force as follows:

recording certain parameters of the dimple-force as the dimple is pressed into the ferrule;

carrying out a preliminary sampling, including keeping records of the parameters as recorded from several completed hoses;

inspecting the several hoses, and determining, in respect of each hose, whether the elastomeric tubing has been properly inserted into the ferrule;

relating that decision to the as-recorded parameters, in respect of each hose, and computing the difference between an accept-value of the parameter, recorded in respect of hoses in which the tubing was properly inserted, and a reject-value of the parameter, recorded in respect of hoses in which the tubing was not properly inserted; and setting the threshold of the dimple-force to a value between the accept-value and the reject-value.

15. As in claim 14, wherein the parameter is the peak magnitude of the dimple-force.

16. As in claim 1, including applying the dimple-force at a high enough magnitude to cause permanent deformation of the metal of the ferrule.

17. As in claim 1, including applying the dimple-force at a low enough magnitude to avoid puncturing right through the metal of the ferrule.

18. As in claim 3, wherein the dimple-pin is at least 3 cm long.

* * * * *